(12) United States Patent
Dhingra et al.

(10) Patent No.: US 6,228,877 B1
(45) Date of Patent: *May 8, 2001

(54) SUBSTITUTED PYRROLES

(75) Inventors: Urvashi Hooda Dhingra, Nutley;
Donna Mary Huryn, Allentown;
Dennis Dalton Keith, Montclair, all of
NJ (US)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/218,404

(22) Filed: Dec. 22, 1998

Related U.S. Application Data

(63) Continuation of application No. 08/900,004, filed on Jul. 24, 1997, now abandoned.
(60) Provisional application No. 60/048,496, filed on Jun. 3, 1997, and provisional application No. 60/022,078, filed on Jul. 29, 1996.

(51) Int. Cl.[7] .................. A61K 31/405; C07D 209/08
(52) U.S. Cl. .............................. 514/414; 548/455
(58) Field of Search ..................... 548/455; 514/414

(56) References Cited

U.S. PATENT DOCUMENTS

| | | |
|---|---|---|
| 5,057,614 | 10/1991 | Davis et al. . |
| 5,380,746 | 1/1995 | Barth et al. . |

FOREIGN PATENT DOCUMENTS

| | | |
|---|---|---|
| 05039289 | 5/1993 | (JP) . |
| WO 93/18765 | 9/1993 | (WO) . |
| WO 93/24491 | 12/1993 | (WO) . |

OTHER PUBLICATIONS

Am. J. Hygiene vol. 27, pp. 493–497, 1938.
Bull. Soc. Chim. Belg. 87 (1978), pp. 229–238.
Sulfur Lett 1983, 1, 167–173.

*Primary Examiner*—Patricia L. Morris
(74) *Attorney, Agent, or Firm*—George W. Johnston; Patricia S. Rocha-Tramaloni; Robert A. Silverman

(57) ABSTRACT

Compounds of the formula

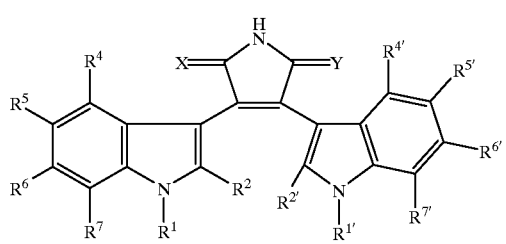

wherein
$R^1$ and $R^{1'}$ are independently alkyl, aryl, alkenyl or alkynyl;
$R^2$ and $R^{2'}$ are independently hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonyl-aminoalkyl, mercaptoalkyl, alkylthioalkyl, carboxyalkyl, alkoxycarbonylalkyl, aminocarbonylalkyl, alkylthio or alkylsulphinyl;
$R^4$, $R^5$, $R^6$, $R^7$, $R^{4'}$, $R^{5'}$, $R^{6'}$, and $R^{7'}$ each independently are hydrogen,

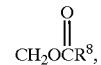

$CO_2R^9$, $CH_2OR^{10}$, $CHO$, $CH_2NR^{11}R^{12}$, $CON(R^{13})_2$, halogen, cyano, aryl, alkyl, hydroxy, alkoxy, aryloxy, haloalkyl, nitro, amino, aralkyloxy, acylamino, monoalkylamino, dialkylamino, thio, alkyl, alkylsulphinyl, alkylsulphonyl, arylsulphinyl, azide, phosphate or phosphonate provided that at least one of $R^4$, $R^5$, $R^6$ and $R^7$ and at least one of $R^{4'}$, $R^{5'}$, $R^{6'}$, and $R^{7'}$ are other than hydrogen, with the proviso that when $R^6$ is methoxy, $R^5$ or $R^{5'}$ are not methoxy;
$R^8$ is alkyl or aryl;
$R^9$ is alkyl or aryl;
$R^{10}$ is hydrogen, alkyl or aryl;
$R^{11}$ and $R^{12}$ are independently hydrogen, alkyl, aryl, aralkyl or acyl;
$R^{13}$ is hydrogen, alkyl, aryl or aralkyl; and
one of X and Y signifies O and the other signifies O, S, (H,OH) or (H,H); as well as pharmaceutically acceptable prodrugs or pharmaceutically acceptable salts of acidic compounds of formula I with bases and or basic compounds of formula I with acids are antiproliferative agents useful in the treatment of cancer.

28 Claims, No Drawings

SUBSTITUTED PYRROLES

This is a Continuation application of Ser. No. 08/900, 004, filed Jul. 24, 1997 now abandoned, which claims priority to Provisional application Ser. Nos. 60/022,078, filed Jul. 29, 1996 and 60/048,496, filed Jun. 3, 1997.

BRIEF SUMMARY OF THE INVENTION

The invention relates to substituted pyrroles. More particularly, the invention relates to substituted pyrroles of the formula

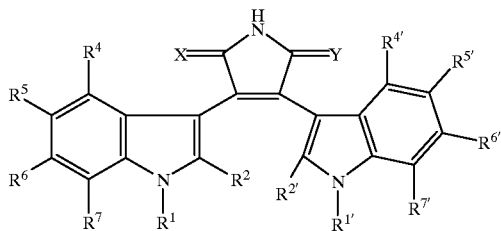

wherein
$R^1$ and $R^{1'}$ are independently alkyl, aryl, alkenyl or alkynyl;
$R^2$ and $R^{2'}$ are independently hydrogen or alkyl;
$R^4, R^5, R^6, R^7, R^{4'}, R^{5'}, R^{6'}$, and $R^{7'}$ each independently are hydrogen,

$CO_2R^9$, $CH_2OR^{10}$, CHO, $CH_2NR^{11}R^{12}$, $CON(R^{13})_2$, halogen, cyano, aryl, alkyl, hydroxy, alkoxy, aryloxy, haloalkyl, nitro, amnino, aralkyloxy, acylamnino, monoalkylarnino, dialkylamino, thio, alkylthio, alkylsulphinyl, alkylsulphonyl, arylsulphinyl, azide, phosphate or phosphonate provided that at least one of $R^4, R^5, R^6$ and $R^7$ and at least one of $R^{4'}, R^{5'}, R^{6'}$, and $R^{7'}$ are other than hydrogen;
$R^8$ is alkyl or aryl;
$R^9$ is alkyl or aryl;
$R^{10}$ is hydrogen, alkyl or aryl;
$R^{11}$ and $R^{12}$ are independently hydrogen, alkyl, aryl, aralkyl or acyl;
$R^{13}$ is hydrogen, alkyl, aryl or aralkyl; and
one of X and Y signifies O and the other signifies O, S, (H,OH) or (H,H); with the proviso that when $R^6$ is methoxy, $R^5$ or $R^{5'}$ can not be methoxy, as well as pharmaceutically acceptable prodrugs or pharmaceutically acceptable salts of acidic compounds of formula I with bases and or basic compounds of formula I with acids.

The compounds of the invention are anti-proliferative agents useful in the treatment or control of cancer, particularly in the treatment or control of solid tumors. The compounds of the invention are especially useful in the treatment or control of breast tumors.

DETAILED DESCRIPTION OF THE INVENTION

The invention relates to substituted pyrroles. More particularly, the invention relates to substituted pyrroles of the formula

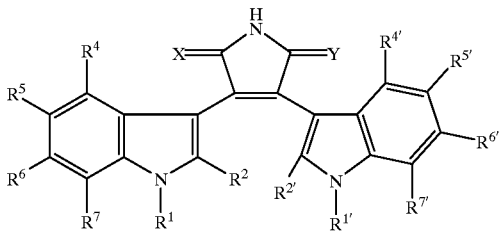

wherein
$R^1$ and $R^{1'}$ are independently alkyl, aryl, alkenyl or alkynyl;
$R^2$ and $R^{2'}$ are independently hydrogen or alkyl;
$R^4, R^5, R^6, R^7, R^{4'}, R^{5'}, R^{6'}$, and $R^{7'}$ each independently are hydrogen,

$CO_2R^9$, $CH_2OR^{10}$, CHO, $CH_2NR^{11}R^{12}$, $CON(R^{13})_2$, halogen, cyano, aryl, aralkyloxy, alkyl, hydroxy, alkoxy, aryloxy, haloalkyl, nitro, amino, aralkyloxy, acylamino, monoalkylamino, dialkylamino, thio, alkylthio, alkylsulphinyl, alkylsulphonyl, arylsulphinyl, azide, phosphate or phosphonate provided that at least one Of $R^4, R^5, R^6$ and $R^7$ and at least one of $R^{4'}, R^{5'}, R^{6'}$, and $R^{7'}$ are other than hydrogen;
$R^8$ is alkyl or aryl;
$R^9$ is alkyl or aryl;
$R^{10}$ is hydrogen, alkyl or aryl;
$R^{11}$ and $R^{12}$ are independently hydrogen, alkyl, aryl, aralkyl or acyl;
$R^{13}$ is hydrogen, alkyl, aryl or aralkyl; and
one of X and Y signifies O and the other signifies O, S, (H,OH) or (H,H); with the proviso that when $R^6$ is methoxy, $R^5$ or $R^{5'}$ are not methoxy, as well as pharmaceutically acceptable prodrugs or pharmaceutically acceptable salts of acidic compounds of formula I with bases and or basic compounds of formula I with acids.

As used herein, the term "alkyl", alone or in combinations, means a straight or branched-chain alkyl group containing a maximum of 10, preferably a maximum of 5, carbon atoms such as methyl, ethyl, propyl, isopropyl, butyl, sec-butyl, t-butyl and pentyl which is unsubstituted or substituted by one or more substituents selected from the group consisting of hydroxy, alkoxy, amino, halogen, thioalkyl or alkylsulphinyl. The term "alkoxy" denotes a group wherein the alkyl residue is as defined above, for example, methoxy, ethoxy, propoxy, isopropoxy, butoxy, t-butoxy and the like. A haloalkyl group can carry one or more halogen atoms, with examples of such groups being chloromethyl and trifluoromethyl. The term "acyl", alone or in combination, means a group derived from an alkanoic acid containing a maximum of 10, preferably a maximum of 5, carbon atoms for example, acetyl, propionyl or butyryl, or from an aromatic carboxylic acid for example, benzoyl. Examples of substituents on alkanoic acid include one or more of the following: hydroxy, alkoxy, amino, halogen, thioalkyl, carboxy, carboxylic acid derivative or alkyl sulphinyl and the like. Examples of substituents on aromatic carboxylic acid include one or more of the following: halogen, alkyl, hydroxy, benzyloxy, alkoxy, haloalkyl, nitro, amino, cyano and the like. The term "aryl", alone or in combinations means an unsubstituted phenyl group or a phenyl group carrying one or more, preferably one to three, substituents, examples of which are halogen, alkyl, hydroxy, benzyloxy, alkoxy, haloalkyl, nitro, amino and cyano. The term "halogen" means fluorine, chlorine, bromine or iodine. The term "amino", alone or in combination means an unsubstituted amine group or an amine substituted by one or more substituents selected from alkyl, aryl, acyl, alkylsulfonyl or arylsulfonyl. The term "alkenyl" refers to straight or branched chain hydrocarbon groups of 2 to 5 carbon atoms having at least one double bond. Groups of 3 to 5 carbon atoms are preferred. The term "alkynyl" refers to straight or branched chain groups of 2 to 5 carbon atoms having at least one triple bond. Groups of 3 to 5 carbon atoms are preferred.

The term "amino protecting group" means any conventional amino protecting group such as alkyl, preferably methyl, substituted alkyl, such as trityl and trialkylsilylethyl, acyl and the like.

As used herein, the term "pharmaceutically acceptable prodrug" means a compound that may be converted under physiological conditions or by solvolysis to a compound of formula I or to a pharmaceutically acceptable salt thereof.

In formula I above, $R^1$ and $R^{1'}$ are preferably alkyl. In an especially preferred embodiment, $R^1$ and $R^{1'}$ are methyl. Preferably, $R^2$ and $R^{2'}$ are hydrogen.

At least one of $R^4$, $R^5$, $R^6$ and $R^7$ and at least one of $R^{4'}$, $R^{5'}$, $R^{6'}$ and $R^{7'}$ are preferably nitro, alkoxy, alkyl, halogen, cyano,

$CO_2R^9$, $CH_2OR^{10}$, $CH_2NR^{11}R^{12}$, CHO, $CON(R^{13})_2$, alkylthio or aralkyloxy.

In a preferred embodiment, at least one of $R^4$, $R^5$, $R^6$, $R^7$ and one of $R^{4'}$, $R^{5'}$, $R^{6'}$ and $R^{7'}$ are cyano,

$CO_2R^9$, $CH_2OR^{10}$, $CH_2NR^{11}R^{12}$, CHO, or $CON(R^{13})_2$.

In a particularly preferred embodiment, one of $R^4$, $R^5$, $R^6$, $R^7$ and one of $R^{4'}$, $R^{5'}$, $R^{6'}$ and $R^{7'}$ are nitro, alkoxy, alkyl, halogen, cyano,

$CO_2R^9$, $CH_2OR^{10}$, $CH_2NR^{11}R^{12}$, CHO, $CON(R^{13})_2$, alkylthio, or aralkyloxy and the others are hydrogen.

In an especially preferred embodiment, $R^6$ and $R^{6'}$ are independently nitro, alkoxy, alkyl, halogen, cyano,

$CO_2R^9$, $CH2OR^{10}$, $CH_2NR^{11}R^{12}$, alkylthio, aralkyloxy, CHO or $CON(R^{13})_2$, and $R^4$, $R^5$, $R^7$ and $R^{4'}$, $R^{5'}$ and $R^{7'}$ are hydrogen.

Preferably $R^8$ and $R^9$ are independently alkyl, particularly preferred is methyl, $R^{10}$ is hydrogen or alkyl, preferably methyl, $R^{11}$ and $R^{12}$ are hydrogen or alkyl and $R^{13}$ is hydrogen or alkyl.

Preferred compounds of formula I are those in which $R^1$ and $R^{1'}$ are alkyl; $R^2$ and $R^{2'}$ are hydrogen, at least one $R^4$, $R^5$, $R^6$ and $R^7$ and at least one of $R^{4'}$, $R^{5'}$ $R^{6'}$ and $R^{7'}$ are nitro, alkoxy, alkyl, halogen, cyano,

$CO_2R^9$, $CH_2OR^{10}$, $CH_2NR^{11}R^{12}$, CHO, $CON(R^{13})_2$, alkylthio, or aralkyloxy, $R^8$ and $R^9$ are alkyl; $R^{10}$ is alkyl; $R^{11}$ and $R^{12}$ are alkyl; and $R^{13}$ is alkyl.

In a particularly preferred embodiment, $R^1$ and $R^{1'}$ are methyl; $R^2$ and $R^{2'}$ are hydrogen, one of $R^4$, $R^5$, $R^6$, $R^7$ and one of $R^{4'}$, $R^{5'}$ $R^{6'}$ and $R^{7'}$ is nitro, alkoxy, alkyl, halogen, cyano,

$CO_2R^9$, $CH_2OR^{10}$, alkylthio, aralkyloxy, $CH_2NR^{11}R^2$, CHO or $CON(R^{13})_2$ and the others are hydrogen; $R^8$ and $R^9$ are methyl; $R^{10}$ is methyl; $R^{11}$ and $R^{12}$ are methyl; and $R^{13}$ is methyl.

In another preferred embodiment, $R^1$ and $R^{1'}$ are alkyl; $R^2$ and $R^{2'}$ are hydrogen, at least one of $R^4$, $R^5$, $R^6$ and $R^7$ is amino, acylamino, monoalkylamino or dialkylamino.

In a particularly preferred embodiment, $R^1$ and $R^{1'}$ are alkyl; $R^2$ and $R^{2'}$ are hydrogen, $R^6$ is amino, acylamino, monoalkylamino or dialkylamino and at least one of $R^{4'}$, $R^{5'}$ and $R^{6'}$ is

$CO_2R^9$, $CH_2OR^{10}$, CHO, $CH_2NR^{11}R^{12}$, $CON(R^{13})_2$, halogen, cyano, aryl, alkyl, hydroxy, alkoxy, aryloxy, haloalkyl, nitro, amino, aralkyloxy, acylamino, monoalkylamino, dialkylamino, thio, alkylthio, alkylsulphinyl, alkylsulphonyl, arylsulphinyl, azide, phosphate or phosphonate.

In a more preferred embodiment, $R^1$ and $R^{1'}$ are alkyl; $R^2$ and $R^{2'}$ are hydrogen, $R^6$ is amino, acylamino, monoalkylamino or dialkylamino and $R^{6'}$ is

$CO_2R^9$, $CH_2OR^{10}$, CHO, $CH_2NR^{11}R^{12}$, $CON(R^{13})_2$, halogen, cyano, aryl, alkyl, hydroxy, alkoxy, aryloxy, haloalkyl, nitro, amino, aralkyloxy, acylamino, monoalkylamino, dialkylamino, thio, alkylthio, alkylsulphinyl, alkylsulphonyl, arylsulphinyl, azide, phosphate or phosphonate; preferably $R^{6'}$ is alkoxy, halogen, cyano, alkylthio, alkyl, nitro or acylamino.

The compounds of formula I in which X and Y both signify O, are prepared by the following Schemes 1–3.

SCHEME 1

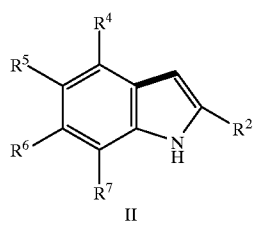

II

↓

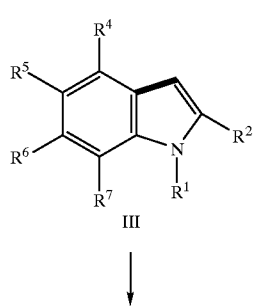

III

↓

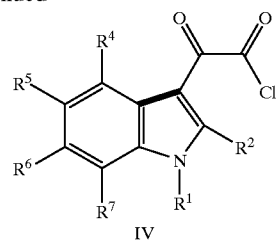

IV wherein $R^1$, $R^2$, $R^4$, $R^5$, $R^6$ and $R^7$ are as described above; provided that when any of $R^1$–$R^7$ are substituents which react with acid chlorides, such as, for example, when any of $R^1$–$R^7$ are hydroxy, hydroxyalkyl, amino, monoalkylamino or aminoalkyl, such substituent is protected with a conventional protecting group.

As set forth in Scheme 1, a compound of formula II, a known compound or compound prepared by known methods, is reacted with NaH and $CH_3I$ in an inert solvent, such as N,N-dimethylformamide or tetrahydrofuran at a temperature of from about 0° C. to about 25° C., to form a corresponding compound of formula III.

A compound of formula III is reacted with oxalyl chloride in a solvent such as diethyl ether ($Et_2O$) or dichloromethane ($CH_2Cl_2$) at a temperature of from 0° C. to 25° C. to form a corresponding compound of formula IV.

SCHEME 2

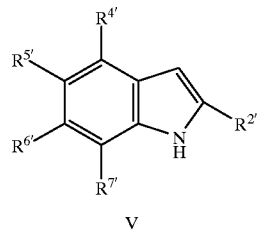

V

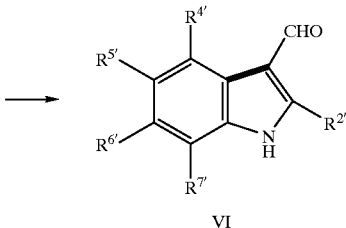

VI

↓

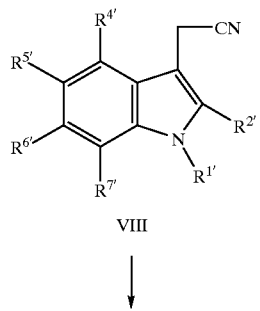

VIII

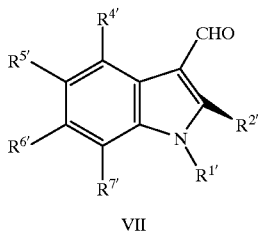

VII

↓

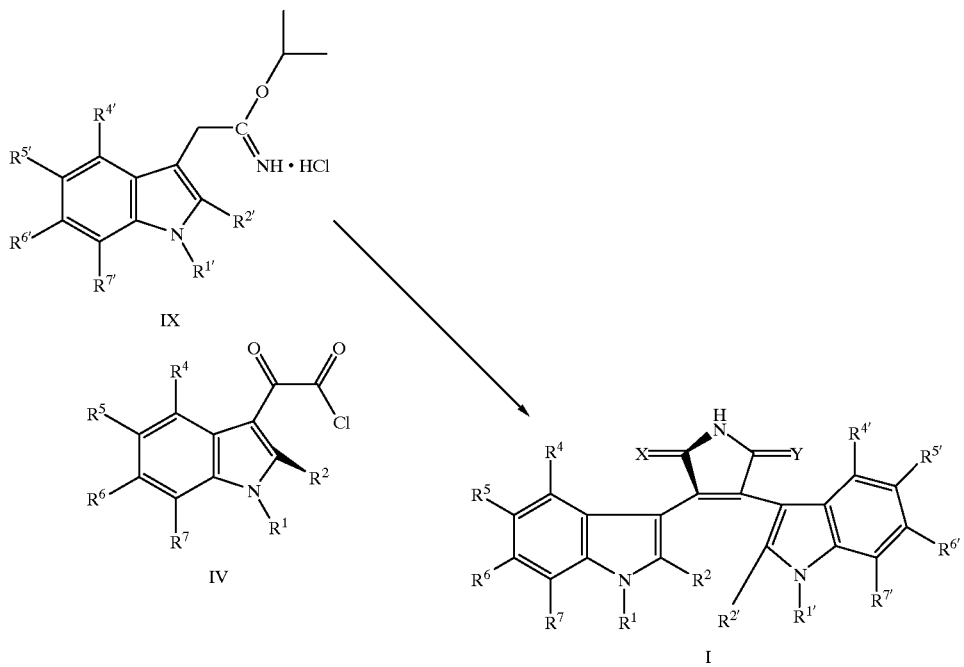

wherein $R^1$, $R^2$, $R^4$, $R^5$, $R^6$, $R^7$, $R^{1'}$, $R^{2'}$, $R^{4'}$, $R^{5'}$, $R^{6'}$ and $R^{7'}$ are as described above; provided that when any of $R^1$–$R^7$ or $R^{1'}$–$R^{7'}$ are substituents, which react with acid chlorides, such as, for example, when any of $R^1$–$R^7$ or $R^{1'}$–$R^{7'}$ are hydroxy, hydroxyalkyl, amino, monoalkylamino or aminoalkyl, such substituent is protected with a conventional protecting group.

As set forth in Scheme 2, a compound of formula V, a known compound or compound prepared by known methods, is reacted with $POCl_3$ in N,N-dimethylformamide (DMF) at a temperature of from 0° C. to 60° C. to form a corresponding compound of formula VI.

A compound of formula VI is reacted with NaH and $CH_3I$ in an inert solvent, such as, dimethylformamide or THF to form a corresponding compound of formula VII.

A compound of formula VII is reacted with potassium tert-butoxide (KOtBu) and toluene-4-sulfonyl methyl isocyanide (TosMIC) in a solvent, such as, ethylene glycoldimethylether (DME) at a temperature between −30° C. and −60° C., then treated with methanol at a temperature of 65° C. to form a corresponding compound of formula VIII.

A compound of formula VIII is reacted with HCl gas in isopropanol to form a corresponding compound of formula IX.

A compound of formula IX is reacted with a compound of formula IV and $Et_3N$ in a solvent such as methylene chloride at a temperature between 0° C. to 25° C. The resultant product is then treated with para-toluene sulphonic acid (pTsOH) in a solvent such as toluene at a temperature of about 25° C. to form a corresponding compound of formula I. If a protecting group was utilized during the reaction of IX and IV, it is removed at this point using methods known in the art.

Alternatively and preferably, to prepare a compound of formula I wherein $R^4$, $R^5$, $R^6$, $R^7$, $R^{4'}$, $R^{5'}$, $R^{6'}$, $R^{7'}$ are amino, alkylamino, dialkylamino or acylamino, a precursor bis-indolylmaleimide of formula I wherein $R^4$, $R^5$, $R^6$, $R^7$, $R^{4'}$, $R^{5'}$, $R^{6'}$ or $R^{7'}$ is nitro, is reduced by methods known in the art to form a corresponding amino bis-indolylmaleimide. The amino group is then modified to the desired alkylamino, dialkyl or acylamino derivative by methods known in the art.

Compounds of formula I wherein $R^1$, $R^2$, $R^4$, $R^5$, $R^6$ and $R^7$ are the same as $R^{1'}$, $R^{2'}$, $R^{4'}$, $R^{5'}$, $R^{6'}$ and $R^{7'}$, respectively can be prepared by the following Scheme 3.

SCHEME 3

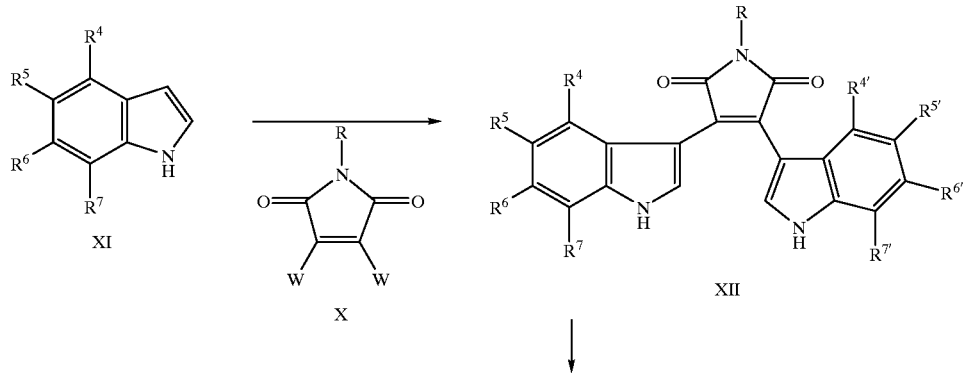

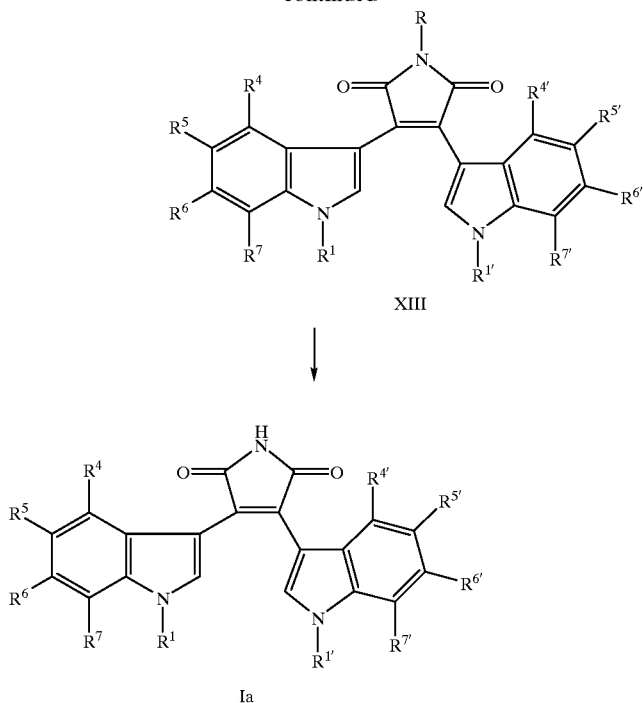

wherein R is an amino protecting group, W is halogen, and $R^1$, $R^2$, $R^4$, $R^5$, $R^6$ and $R^7$ are the same as $R^{1'}$, $R^{2'}$, $R^{4'}$, $R^{5'}$, $R^{6'}$ and $R^{7'}$ respectively and are as described above.

As set forth in Scheme 3, a compound of formula XI, a known compound or compound prepared by known methods, is reacted with a compound of formula X, a known compound or compound prepared by known methods, and a base such as methylmagnesium iodide and a base such as sodium hydride in a solvent such as toluene at a temperature of between 25° C. and the reflux temperature of the solvent to form a corresponding compound of formula XII.

A compound of formula XII is reacted with a base such as potassium carbonate and an alkylating agent such as $CH_3I$ in a solvent such as N-methylpyrrolidinone at room temperature to form a corresponding compound of formula XIII.

The protecting group R is removed to form a corresponding compound of formula Ia by conventional methods which may include reaction of a compound of formula XIII with potassium hydroxide in a solvent such as ethanol, followed by treatment with a mixture of 1,1,1,3,3,3-hexamethyldisilazane and methanol in a solvent such as DMF at room temperature.

A compound of formula I in which one of X and Y signifies O and the other signifies S, is prepared by reacting a compound of formula I in which X and Y both signify O with a sulphurizing agent.

Conventional procedures can be used in carrying out the sulfurization, including the protection of substituents prior to sulfurization and deprotection after sulfurization, which would be known to those skilled in the art.

The sulfurization is conveniently carried out using phosphorous pentasulfide, Lawesson's reagent [2,4-bis(4-methoxyphenyl)-1,2-dithioxo-1,3,2,4-dithiaphosphetane: Bull. Soc. Chim. Belg. 87 (1978) 229–238] or Davy reagent [2,4-bis(methylthio)-1,3,2,4-dithiadiphosphetane; Sulfur Lett. 1983, 1, 167]. This reaction is expediently carried out in an inert organic solvent such as an aliphatic or cyclic ether (for example, dimethoxyethane) or an aromatic hydrocarbon which may be halogenated (for example, benzene, toluene or chlorobenzene) and at an elevated temperature, especially at the reflux temperature of the reaction mixture.

A compound of formula I in which one of X and Y signifies O and the other signifies (H,OH), is prepared by reducing a compound of formula I in which X and Y both signify O with a complex metal hydride.

The reduction can be carried out in a known manner including the protection of substituents on the indole ring prior to reduction and deprotection after reduction according to known methods. An alkali metal aluminum hydride such as lithium aluminum hydride is preferably used as the complex metal hydride, although other hydrides such as diisobutylaluminum hydride and sodium dihydro-bis(2-methoxy-ethoxy)aluminate can also be used. Suitable inert organic solvents in which this reduction can be carried out include aliphatic and cyclic ethers such as diethyl ether or tetrahydrofuran (THF) and hydrocarbons such as hexane, benzene and toluene. Conveniently, this reduction is carried out at about room temperature.

A compound of formula I in which one of X and Y signifies O and the other signifies (H,H), can be prepared by catalytically hydrogenating a compound of formula I in which one of X and Y signifies O and the other signifies (H,OH).

Conventional procedures can be used in carrying out the catalytic hydrogenation including the protection and deprotection of substituents on the indole ring according to known procedures. Thus, the catalytic hydrogenation can be carried out in the presence of a noble metal catalyst such as a palladium or platinum catalyst, for example, palladium/carbon (Pd/C), and an inert organic solvent such as an alkanol (for example, methanol or ethanol). This catalytic hydrogenation is expediently carried out at about room temperature and under atmospheric pressure.

If desired, an acidic compound of formula I can be converted into a pharmaceutically acceptable salt with a base or a basic compound of formula I can be converted into a pharmaceutically acceptable salt with an acid.

The conversion of an acidic compound of formula I into a pharmaceutically acceptable salt can be carried out by treatment with a suitable base in a known manner. Suitable salts are those derived not only from inorganic bases, for example, sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a known manner. Suitable salts are those derived not only from inorganic acids, for example, hydrochlorides, hydrobromides, phosphates or sulphates, but also from organic acids, for example, acetates, citrates, fumarates, tartrates, maleates, methanesulphonates or p-toluenesulphonates.

The pyrroles of formula I and their pharmaceutically acceptable salts inhibit cellular processes, for example cell proliferation, and can be used in the treatment or control of inflammatory disorders such as arthritis, immune diseases, in conjunction with organ transplants and in oncology.

The epithelial breast carcinoma cell line (MDAMB-435) was purchased from ATCC (American Type Cell Culture Collection) and was grown in culture in medium as recommended by ATCC. For analysis of the effect of various compounds on growth of these cells, the cells were plated at a concentration of 1500 cells/well in a 96 well tissue culture plate ("test plate). The day after the cells were plated, the compounds to be analyzed were dissolved in 100% DMSO (dimethyl sulfoxide) to yield at 10 mM stock solution. Each compound was diluted in $H_2O$ to 1 mM and was added to triplicate wells in the first row of a 96 well master plate which contains medium to yield a final concentration of 40 $\mu$M. The compounds were then serially diluted in medium in the "master plate". The diluted compound(s) were then transferred to test plates containing cells. A row of vehicle "control cells" received DMSO. The final concentration of DMSO in each well was 0.1%. 5 days post drug addition, the plate was analyzed as follows:

MTT (3-(4–5 methyl thiazole-2-yl)-2,5-diphenyl tetrazolium bromide; thiazolyl blue) was added to each well to yield a final concentration of 1 mg/ml. The plate was then incubated at 37° C. for 2½–3 hours. The MTT containing medium was then removed and 50 $\mu$l of 100% ethanol was added to each well to dissolve the formazan. The absorbences were then read using an automated plate reader (Bio-tek microplate reader).

$IC_{50}$'s were calculated using the Reed and Munsch equation, see Am. J. Hygiene Vol. 27 pgs. 493–497, 1938.

The results are provided in the Table below for compounds of formula Ia.

TABLE

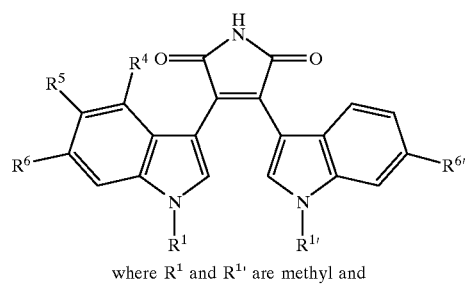

Ia where $R^1$ and $R^{1'}$ are methyl and

| $R^4$ | $R^5$ | $R^6$ | $R^{6'}$ | $IC_{50}(\mu M)$ |
|---|---|---|---|---|
| H | H | $OCH_3$ | $NO_2$ | 0.007 |
| H | H | $CH_3$ | $OCH_3$ | 0.02 |

TABLE-continued

Ia where $R^1$ and $R^{1'}$ are methyl and

| $R^4$ | $R^5$ | $R^6$ | $R^{6'}$ | $IC_{50}(\mu M)$ |
|---|---|---|---|---|
| H | H | $CH_3$ | $NO_2$ | 0.07 |
| H | H | $NO_2$ | $SCH_3$ | 0.009 |
| H | H | $NO_2$ | Obenzyl | 0.09 |
| H | H | $NO_2$ | Cl | 0.07 |
| H | H | $OCH_3$ | $OCH_3$ | 0.005 |
| H | H | $NO_2$ | F | 0.07 |
| H | H | $NO_2$ | $NO_2$ | 0.07 |
| H | H | F | $OCH_3$ | 0.02 |
| H | H | Cl | $OCH_3$ | 0.007 |
| H | H | $CO_2CH_3$ | $NO_2$ | 0.007 |
| H | H | CN | $NO_2$ | 0.05 |
| H | H | $CH_3$ | CN | 0.01 |
| H | H | CN | $OCH_3$ | 0.005 |
| H | H | $CH_3S$ | $NO_2$ | 0.009 |
| H | H | Br | $NO_2$ | 0.07 |
| H | H | $N_3$ | $CH_3O$ | 0.07 |
| H | H | $Et(OCH_2CH_2)_2O$ | $NO_2$ | 0.04 |
| H | H | $NH_2$ | CN | <0.01 |
| H | H | $NH_2$ | $NH_2$ | 0.7 |
| H | H | $NH_2$ | F | 0.042 |
| H | H | $NH_2$ | Cl | 0.012 |
| H | H | $NH_2$ | Br | 0.004 |
| H | H | $NH_2$ | $CO_2CH_3$ | 0.05 |
| H | H | $NH_2$ | $CH_3O$ | 0.015 |
| H | H | $NH_2$ | EtO | 0.012 |
| H | H | $NH_2$ | $NO_2$ | <0.01 |
| H | H | $CH_3CONH$ | $NO_2$ | 0.02 |
| H | H | $CF_3CONH$ | $NO_2$ | 0.012 |
| H | H | CHONH | $CH_3O$ | 0.01 |
| H | H | $CH_3CONH$ | $CH_3O$ | 0.07 |
| H | H | $CH_3NH$ | $CH_3O$ | <0.01 |
| H | CN | H | $CH_3$ | 0.4 |
| H | $CH_3$ | H | $NO_2$ | 0.13 |
| H | CN | H | $NO_2$ | 1.0 |
| H | Cl | H | $NO_2$ | 0.17 |
| H | $NO_2$ | H | $NO_2$ | 0.83 |
| H | $CH_3O$ | H | $CH_3O$ | 0.07 |
| H | $CH_3O$ | H | CN | 0.07 |
| H | $CH_3O$ | H | Cl | 0.2 |
| H | $CH_3O$ | H | $CH_3S$ | 0.2 |
| H | $CH_3O$ | H | EtO | 0.07 |
| H | $CH_3$ | H | $CH_3$ | 0.4 |
| H | Cl | H | $CH_3$ | 0.4 |
| $CH_3O$ | H | H | $NO_2$ | 0.4 |
| $CH_3O$ | H | H | $CH_3O$ | 0.07 |
| F | H | H | $CH_3O$ | 0.2 |
| F | H | H | $NO_2$ | 0.05 |
| F | H | H | EtO | 0.032 |
| Br | H | H | EtO | 0.2 |

The pyrroles of formula I and their aforementioned salts can be used as medicaments, for example, in the form of pharmaceutical preparations, which can be administered orally, for example, in the form of tablets, coated tablets, dragees, hard or soft gelatin capsules, solutions, emulsions or suspensions. They can also be administered rectally, for example, in the form of suppositories or parenterally, for example, in the form of injection solutions.

For the manufacture of pharmaceutical preparations these compounds can be formulated with therapeutically inert, inorganic or organic carriers. Lactose, maize starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid polyols. Depending on the nature of the active substance no carriers are, however, generally required in the case of soft gelatin capsules. Suitable carriers for the manufacture of solutions and syrups are, water, polyols, saccharose, invert sugar and glucose. Suitable carriers for injection solutions are water, alcohols, polyols, glycerine and vegetable oils. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, the pyrroles of formula I and their aforementioned salts can be used in the treatment or control of oncological, inflammatory, immunological, bronchopulmonary and cardiovascular disorders. The dosage can vary within wide limits and will, or course, be adjusted to the individual requirements in each particular case. In general, in the case of oral or parenteral administration to adult humans, a daily dosage of about 5mg to 5000 mg should be appropriate, although the upper limit may be exceeded when this is found to be expedient. The daily dosage can be administered as a single dose or in divided doses, or for parenteral administration, it may be given as continuous infusion.

The following Examples illustrate the present invention:

EXAMPLE 1

3-(6-methoxy-1-methyl-1H-indol-3-yl)-4-(1-methyl-6-nitro-1H-indol-3-yl)-pyrrole-2,5-dione a) A solution of known 6-nitro-1H-indole (5 g, 31 mm) in dimethylformamide (DMF) (50 mL) was cooled to 0° C. and treated with NaH (1 g, 37m). After stirring at 0° C. for two hours, CH$_3$I (2.3 mL, 37 mm) was added, and the reaction was stirred overnight while allowing to warm to room temperature. After pouring into H$_2$O (500 mL), the mixture was extracted with ethyl acetate (EtOAc) (200 mL×4). The combined organic fractions were dried over MgSO$_4$, filtered and evaporated. Purification by flash column chromatography afforded the 1-methyl-6-nitro-1H-indole (5.34 g, 97%).

b) A stirred solution of 1-methyl-6-nitro-1H-indole in diethyl ether (Et$_2$O) (5 mL) was cooled to 0° C., and treated with oxalyl chloride (0.15 mL, 1.7 mm). After stirring at room temperature overnight, solids were collected, washed with ether and dried to afford (255 mg, 96%) (1-methyl-6-nitro-1H-indol-3-yl)-oxo-acetyl chloride.

c) A mixture of DMF (7 mL, 90 mm) and POCl$_3$ (2.25 mL, 24.5 mmol) which had been cooled to 5° C., was treated with known 6-methoxy-1H-indole. After stirring at room temperature for 1 hour, the mixture was heated at 45° C. for 1 hour, then allowed to cool to room temperature overnight. The reaction mixture was poured into ice (100 mL), and stirred for 30 minutes at which time a solution of KOH (9.6 g, 171 mm) in H$_2$O (20 mL) was added dropwise. After stirring for 30 minutes, then heating for 1 hour at 60° C., the reaction was cooled to 30° C., and the pH adjusted to 7 with 1N HCl. The mixture was extracted with EtOAc (50 mL×3), the organic fractions were combined, dried over MgSO$_4$, filtered and evaporated. The residue was purified by crystallization from methanol to afford 6-methoxy-1H-indole-3-carboxaldehyde (1.65 g, 69%).

d) A solution of 6-methoxy-1H-indole-3-carboxaldehyde (1.65, 9.4 mm) in DMF (10 mL) was cooled to 0° C., and treated with NaH(11.3 mm). After stirring at room temperature for 1 hour, the mixture was cooled to 0° C., treated with CH$_3$I (0.7 mL, 11.3 mm), then allowed to warm to room temperature overnight. After pouring into H$_2$O (200 mL), the mixture was acidified with HCl and extracted with EtOAc (100 mL×2). The combined organic fractions were dried over MgSO$_4$, filtered and evaporated to afford 6-methoxy-1-methyl-1H-indole-3-carboxaldehyde (1.78 g, 99%).

e) To a cooled (−30° C.) suspension of potassium tert-butoxide (KOtBu) (1.62 g, 14.4 mm) in dimethoxyethane (DME; 25 mL) was added a solution oftoluene-4-sulfonylmethyl isocyanide TosMIC (1.45 g, 7.4 mmol) in DME (15 mL). After cooling the mixture further to −60° C., a solution of 6-methoxy-1-methyl-1H-indole-3-carboxaldehyde (800 mg, 4.23 mm) was slowly added, and the reaction mixture stirred for 1.5 hours. After treatment with methanol (11 mL), the mixture was heated to reflux temperature for 15 minutes, then the solvent evaporated. The residue was treated with H$_2$O (15 mL) which contained acetic acid (HOAc) (55 mL), then extracted with CH$_2$Cl$_2$ (50 mL×3). The combined organic layers were washed with saturated NaHCO$_3$ solution (50 mL), dried over MgSO$_4$, filtered and evaporated. Purification by flash column chromatography afforded (6-methoxy-1-methyl-1H-indol-3-yl)acetonitrile (0.6 g, 70%).

f) HCl gas was bubbled into a suspension of (6-methoxy-1-methyl-1H-indol-3-yl)acetonitrile in isopropanol (25 mL) which was cooled to 0° C. After 3 hours, the solvent was evaporated and the residue evaporated from diethyl ether (Et$_2$O) (50 mL×2). The tan residue was further dried under high vacuum to afford 2-(6-methoxy-1-methyl-1H-indol-3-yl)-acetimidic acid isopropyl ester hydrochloride (1.6 g, 82%).

g) A suspension of (1-methyl-6-nitro-1H-indol-3-yl)-oxo-acetyl chloride (251 mg, 0.94 mm) and 2-(6-methoxy-1-methyl-1H-indol-3-yl)-acetimidic acid isopropyl ester hydrochloride (280 mg, 0.94 mm) in CH$_2$Cl$_2$(25 mL) was cooled to 0° C., treated with Et$_3$N (0.53 mL, 3.7 mm), and stirred at room temperature while allowing to warm to room temperature overnight. The mixture was then diluted with CH$_2$Cl$_2$ (25 mL), washed with H$_2$O (20 mL), and 0.5 N HCl (20 mL). The combined organic layers were dried over MgSO$_4$, filtered and evaporated. The residue was then combined with toluene (4 mL), cooled to 0° C., treated with pTsOH (197 mg, 1 mm), and stirred for 3 hours. The red solids which precipitated were collected and partitioned between CH$_2$Cl$_2$ (50 mL), and H$_2$O (25 mL). The organic fraction was washed with saturated NaHCO$_3$ solution (25 mL), then dried over MgSO$_4$, filtered and evaporated. Rinsing the residue with tetrahydrofuran (THF) afforded 3-(6-methoxy-1-methyl-1H-indol-3-yl)-4-(1-methyl-6-nitro-1H-indol-3yl)-pyrrole-2,5-dione; mp=308–310° C.; in 31% yield.

EXAMPLE 2

In a manner similar to that described in Example 1(g), the following compounds were prepared. The starting materials were prepared in a manner analogous to that described in 1 (b) and 1 (f).

a) 3-(6-benzyloxy-1-methyl-1H-indol-3-yl)-4-(1-methyl-6-nitro-1H-indol-3-yl)-pyrrole-2,5-dione; mp=160–165° C.

was prepared from (6-benzyloxy-1-methyl-1H-indol-3-yl)-oxo-acetyl chloride and 2-(1-methyl-6-nitro-1H-indol-3-yl)-acetimidic acid isopropyl ester hydrochloride.

b) 3-(6-chloro-1-methyl-1H-indol-3-yl)-4-(1-methyl-6-nitro-1H-indol-3-yl)-pyrrole-2,5-dione; mp=300–302° C. was prepared from (6-chloro-1-methyl-1H-indol-3-yl)-oxo-acetyl chloride and 2-(1-methyl-6-nitro-1H-indol-3-yl)-acetimidic acid isopropyl ester hydrochloride.

c) 3-(1,6-dimethyl-1H-indol-3-yl)-4-(6-methoxy-1-methyl-1H-indol-3-yl)-pyrrole-2,5-dione; mp=240–245° C.; was prepared from (6-methoxy-1-methyl-1H-indol-3-yl)-oxo-acetyl chloride and 2-(1,6-dimethyl-1H-indol-3-yl)-acetimidic acid isopropyl ester hydrochloride.

d) 3-(1,6-dimethyl-1H-indol-3-yl)-4-(1-methyl-6-nitro-1H-indol-3-yl)-pyrrole-2,5-dione; mp=268–272° C.; was prepared from (1-methyl-6-nitro-1H-indol-3-yl)-oxo-acetyl chloride and 2-(1,6-dimethyl-1H-indol-3-yl)-acetimidic acid isopropyl ester hydrochloride.

e) 3,4-Bis-(6-methoxy-1-methyl-1H-indol-3-yl)-pyrrole-2,5-dione; mp=258–260° C.; was prepared from (6-methoxy-1-methyl-1H-indol-3-yl)-oxo-acetyl chloride and 2-(6-methoxy-1-methyl-1H-indol-3-yl)-acetimidic acid isopropyl ester hydrochloride.

f) 3-(6-fluoro-1-methyl-1H-indol-3-yl)-4-(1-methyl-6-nitro-1H-indol-3-yl)-pyrrole-2,5-dione; mp=270–272° C.; was prepared from (6-fluoro-1-methyl-1H-indol-3-yl)-oxo-acetyl chloride and 2-(1-methyl-6-nitro-1H-indol-3-yl)-acetimidic acid isopropyl ester hydrochloride.

g) 3,4-Bis-(1-methyl-6-nitro-1H-indol-3-yl)-pyrrole-2,5-dione; mp>360° C.; was prepared from (1-methyl-6-nitro-1H-indol-3-yl)-oxo-acetyl chloride and 2-(1-methyl-6-nitro-1H-indol-3-yl)-acetimidic acid isopropyl ester hydrochloride.

h) 3-(6-fluoro-1-methyl-1H-indol-3-yl)-4-(6-methoxy-1-methyl-1H-indol-3-yl)-pyrrole-2,5-dione; mp=255–257° C.; was prepared from (6-fluoro-1-methyl-1H-indol-3-yl)-oxo-acetyl chloride and 2-(6-methoxy-1-methyl-1H-indol-3-yl)-acetimidic acid isopropyl ester hydrochloride.

i) 3-(6-chloro-1-methyl-1H-indol-3-yl)-4-(6-methoxy-1-methyl-1H-indol-3-yl)-pyrrole-2,5-dione; mp=283–285° C.; was prepared from (6-chloro-1-methyl-1H-indol-3-yl)-oxo-acetyl chloride and 2-(6-methoxy-1-methyl-1H-indol-3-yl)-acetimidic acid isopropyl ester hydrochloride.

j) 1-methyl-3[4-(1-methyl-6-nitro-1H-indol-3-yl)-2,5-dioxo-2,5-dihydro-1H-pyrrole-3-yl]-1H-indole-6-carboxylic acid methyl ester; mp=294–296° C.; was prepared from 3-chlorocarbone-carbonyl-1-methyl-1H-indole-6-carboxylic acid methyl ester and 2-(1-methyl-6-nitro-1H-indol-3-yl)-acetimidic acid isopropyl ester hydrochloride.

k) 1-methyl-3-[4-(1-methyl-6-nitro-1H-indol-3-yl)-2,5-dioxo-2,5-dihydro-1H-pyrrol-3-yl]1H-indole-6-carbonitrile; mp=253–255° C.(d) was prepared from (6-cyano-1-methyl-1H-indol-3-yl)-oxo-acetyl chloride and 2-(1-methyl-6-nitro-1H-indol-3-yl)-acetimidic acid isopropyl ester hydrochloride.

l) 3-[4-(1,6-dimethyl-1H-indol-3-yl)-2,5-dioxo-2,5-dihydro-1H-pyrrole-3-yl]-1-methyl-1H-indole-6-carbonitrile; mp=310–312° C. was prepared from (6-cyano-1-methyl-1H-indol-3-yl)-oxo-acetyl chloride and 2-(1,6-dimethyl-1H-indol-3-yl)-acetimidic acid isopropyl ester hydrochloride.

m) 3-[4-(6-methoxy-1-methyl-1H-indol-3-yl)-2,5-dioxo-2,5-dihydro-1H-pyrrole-3-yl]-1-methyl-indol-6-carbonitrile; mp=261–263° C. was prepared from (6-cyano-1-methyl-1H-indol-3-yl)-oxo-acetyl chloride and 2-(6-methoxy-1-methyl-1H-indol-3-yl)-acetimidic acid isopropyl ester hydrochloride.

n) 3-(1-Methyl-6-methylsulfanyl-1H-indol-3-yl)-4-(1-methyl-6-nitro-1H-indol-3-yl)-pyrrole-2,5-dione; mp=273–275° C. was prepared from (1-methyl-6-methylsulfanyl-1H-indol-3-yl)-oxo-acetyl chloride and 2-(1-methyl-6-nitro-1H-indol-3-yl)-acetimidic acid isopropyl ester hydrochloride.

o) 3-(6-Bromo-1-methyl-1H-indol-3-yl)-4-(1-methyl-6-nitro-1H-indol-3-yl)-pyrrole-2,5-dione; mp=319–321° C. was prepared from (6-bromo-1-methyl-1H-indol-3-yl)-oxo-acetyl chloride and 2-(1-methyl-6-nitro-1H-indol-3-yl)-acetimidic acid isopropyl ester hydrochloride.

p) 3-(6-Iodo-1-methyl-1H-indol-3-yl)-4-(1-methyl-6-nitro-1H-indol-3-yl)-pyrrole-2,5-dione; mp=317–321° C. was prepared from (6-iodo-1-methyl-1H-indol-3-yl)-oxo-acetyl chloride and 2-(1-methyl-6-nitro-1H-indol-3-yl)-acetimidic acid isopropyl ester hydrochloride.

q) 3-(6-Azido-1-methyl-1H-indol-3-yl)-4-(6-methoxy-1-methyl-1H-indol-3-yl)-pyrrole-2,5,-dione was prepared from (6-azido-1-methyl-1H-indol-3-yl)-oxo-acetyl chloride and 2-(6-methoxy-1-methyl-1H-indol-3-yl)-acetimidic acid isopropyl ester hydrochloride.

r) 3-(4-Methoxy-1-methyl-1H-indol-3-yl)-4-(1-methyl-6-nitro-1H-indol-3-yl)-pyrrole-2,5-dione; mp=290–292° C. was prepared from (4-methoxy-1-methyl-1H-indol-3-yl)-oxo-acetyl chloride and 2-(1-methyl-6-nitro-1H-indol-3-yl)-acetimidic acid isopropyl ester hydrochloride.

s) 3-(6-Methoxy-1-methyl-1H-indol-3-yl)-4-(4-methoxy-1-methyl-1H-indol-3-yl)-pyrrole-2,5-dione; mp=270–273° C. was prepared from (4-methoxy-1-methyl-1H-indol-3-yl)-oxo-acetyl chloride and 2-(6-methoxy-1-methyl-1H-indol-3-yl)-acetimidic acid isopropyl ester hydrochloride.

t) 3-(4-Fluoro-1-methyl-1H-indol-3-yl)-4-(6-methoxy-1-methyl-1H-indol-3-yl)-pyrrole-2,5-dione; mp=283–285° C. was prepared from (4-fluoro-1-methyl-1H-indol-3-yl)-oxo-acetyl chloride and 2-(6-methoxy-1-methyl-1H-indol-3-yl)-acetimidic acid isopropyl ester hydrochloride.

u) 3-(4-Fluoro-1-methyl-1H-indol-3-yl)-4-(1-methyl-6-nitro-1H-indol-3-yl)-pyrrole-2,5-dione was prepared from (4-fluoro-1-methyl-1H-indol-3-yl)-oxo-acetyl chloride and 2-(1-methyl-6-nitro-1H-indol-3-yl)-acetimidic acid isopropyl ester hydrochloride.

v) 3-[4-(5-methoxy-1-methyl-1H-indol-3-yl)-2,5-dioxo-2,5-dihydro-1H-pyrrol-3-yl]-1-methyl-1H-indole-6-carbonitrile; mp=326–328° C. was prepared from (6-cyano-1-methyl-1H-indol-3-yl)-oxo-acetyl chloride 2-(5-methoxy-1-methyl-1H-indol-3-yl)-acetimidic acid isopropyl ester hydrochloride.

w) 3-(6-Chloro-1-methyl-1H-indol-3-yl)-4-(5-methoxy-1-methyl-1H-indol-3-yl)-pyrrole-2,5-dione; mp=289–292° C. was prepared from (6-chloro-1-methyl-1H-indol-3-yl)-oxo-acetyl chloride and 2-(5-methoxy-1-methyl-1H-indol-3-yl)-acetimidic acid isopropyl ester hydrochloride.

x) 3-(5-Methoxy-1-methyl-11H-indol-3-yl)-4-(1-methyl-6-methylsulfanyl-1H-indol-3-yl)-pyrrole-2,5-dione; mp=261–264° C. was prepared from (1-methyl-6-methylsulfanyl-1H-indol-3-yl)-oxo-acetyl chloride and 2-(5-methoxy-1-methyl-1H-indol-3-yl)-acetimidic acid isopropyl ester hydrochloride.

y) 3-(6-Ethoxy-1-methyl-1H-indol-3-yl)-4-(5-methoxy-1-methyl-1H-indol-3-yl)-pyrrole-2,5-dione; mp=229–232° C. was prepared from (6-ethoxy-1-methyl-1H-indol-3-yl)-oxo-acetyl chloride and 2-(5-methoxy-1-methyl-1H-indol-3-yl)-acetimidic acid isopropyl ester hydrochloride.

z) 3-(1,6-Dimethyl-1H-indol-3-yl)-4-(1,5-dimethyl-1H-indol-3-yl)-pyrrole-2,5-dione; mp=248–250° C. was prepared from (1,6-dimethyl-1H-indol-3-yl)-oxo-acetyl chloride 2-(1,5-dimethyl-1H-indol-3-yl)-acetimidic acid isopropyl ester hydrochloride.

aa) 3-(5-Chloro-1-methyl-1H-indol-3-yl)-4-(1,6-dimethyl-1H-indol-3-yl)-pyrrole-2,5-dione; mp=247–249° C. was prepared from (5-chloro-1-methyl-1H-indol-3-yl)-oxo-acetyl chloride and 2-(1,6-dimethyl-1H-indol-3-yl)-acetimidic acid isopropyl ester hydrochloride.

bb) 3-[4-(1,6-Dimethyl-1H-indol-3-yl]-2,5-dioxo-2,5-dihydro-1H-pyrrol-3-yl] 1-methyl-1H-indole-5-carbonitrile; mp=269–271° C. was prepared from (5-cyano-1-methyl-1H-indol-3-yl)-oxo-acetyl chloride and 2-(1,6-dimethyl-1H-indol-3-yl)-acetimidic acid isopropyl ester hydrochloride.

cc) 3-(1,5-Dimethyl-1H-indol-3-yl)-4-(1-methyl-6-nitro-1H-indol-3-yl)-pyrrole-2,5-dione; mp=248–250° C. was prepared from (1,5-dimethyl-1H-indol-3-yl)-oxo-acetyl chloride and 2-(1-methyl-6-nitro-1H-indol-3-yl)-acetimidic acid isopropyl ester hydrochloride.

dd) 1-Methyl-3-[4-(1-methyl-6-nitro-1H-indol-3-yl)-2,5-dioxo-2,5-dihydro-1H-pyrrol-3-yl]-1H-indole-5-carbonitrile; mp=257–260° C. was prepared from (5-cyano-1-methyl-1H-indol-3-yi)-oxo-acetyl chloride and 2-(1-methyl-6-nitro-1H-indol-3-yl)-acetimidic acid isopropyl ester hydrochloride.

ee) 3-(5-Chloro-1-methyl-1H-indol-3-yl)-4-(1-methyl-6-nitro-1H-indol-3-yl)-pyrrole-2,5-dione; mp=301–303° C. was prepared from (5-chloro-1-methyl-1H-indol-3-yl)-oxo-acetyl chloride and 2-(1-methyl-6-nitro-1H-indol-3-yl)-acetimidic acid isopropyl ester hydrochloride.

ff) 3-(1-methyl-5-nitro-1H-indol-3-yl)-4-(1-methyl-6-nitro-1H-indol-3-yl)-pyrrole-2,5-dione; mp=270° C. was prepared from (1-methyl-5-nitro-1H-indol-3-yl)-oxo-acetyl chloride and 2-(1-methyl-6-nitro-1H-indol-3-yl)-acetimidic acid isopropyl ester hydrochloride.

gg) 3-(5-Methoxy-1-methyl-1H-indol-3-yl)-4-(4-methoxy-1-methyl-1H-indol-3-yl)-pyrrole-2,5-dione; mp=250–254° C. was prepared from (4-methoxy-1-methyl-1H-indol-3-yl)-oxo-acetyl chloride and 2-(5-methoxy-1-methyl-1H-indol-3-yl)-acetimidic acid isopropyl ester hydrochloride.

hh) 3,4-Bis-(5-methoxy-1-methyl-1H-indol-3-yl)-pyrrole-2,5-dione; mp=236–238° C. was prepared from (5-methoxy-1-methyl-1H-indol-3-yl)-oxo-acetyl chloride and 2-(5-methoxy-1-methyl-1H-indol-3-yl)-acetimidic acid isopropyl ester hydrochloride.

ii) 3-(1,5-Dimethyl-1H-indol-3-yl)-4-(5-methoxy-1-methyl-1H-indol-3-yl)-pyrrole-2,5-dione; mp=217–220° C. was prepared from (1,5-dimethyl-1H-indol-3-yl)-oxo-acetyl chloride and 2-(5-methoxy-1-methyl-1H-indol-3-yl)-acetimidic acid isopropyl ester hydrochloride.

jj) 3-(5-Chloro-1-methyl-1H-indol-3-yl)-4-(5-methoxy-1-methyl-1H-indol-3-yl)-pyrrole-2,5-dione; mp=245–248° C. was prepared from (5-chloro-1-methyl-1H-indol-3-yl)-oxo-acetyl chloride and 2-(5-methoxy-1-methyl-1H-indol-3-yl)-acetimidic acid isopropyl ester hydrochloride.

kk) 3-[4-(5-Methoxy-1-methyl-1H-indol-3-yl)-2,5-dioxo-2,5-dihydro-1H-pyrrol-3-yl]-1-methyl-1H-indole-5-carbonitrile; mp=252–255° C. was prepared from (5-cyano-1-methyl-1H-indol-3-yl)-oxo-acetyl chloride and 2-(5-methoxy-1-methyl-1H-indol-3-yl)-acetimidic acid isopropyl ester hydrochloride.

ll) 3-(1-Methyl-6-nitro-1H-indol-3-yl)-4-(1-methyl-7-nitro-1H-indol-3-yl)-pyrrole-2,5-dione was prepared from (1-methyl-6-nitro-1H-indol-3-yl)-oxo-acetyl chloride and 2-(1-methyl-7-nitro-1H-indol-3-yl)-acetimidic acid isopropyl ester hydrochloride.

mm) 3-(6-Fluoro-1-methyl-1H-indol-3-yl)-4-(1-methyl-7-nitro-1H-indol-3-yl)-pyrrole-2,5-dione was prepared from (6-Fluoro-1-methyl-1H-indol-3-yl)-oxo-acetyl chloride and 2-(1-methyl-7-nitro-1H-indol-3-yl)-acetimidic acid isopropyl ester hydrochloride.

nn) 3-(1,6-Dimethyl-1H-indol-3-yl)-4-(1-methyl-7-nitro-1H-indol-3-yl)-pyrrole-2,5-dione; mp=259–261° C. was prepared from (1-methyl-7-nitro-1H-indol-3-yl)-oxo-acetyl chloride and 2-(1,6-dimethyl-1H-indol-3-yl)-acetimidic acid isopropyl ester hydrochloride.

oo) 3-(4-Fluoro-1-methyl-1H-indol-3-yl)-4-(6-ethoxy-1-methyl-1H-indol-3-yl)-pyrrole-2,5-dione; mp=>280° C. was prepared from (4-fluoro-1-methyl-1H-indol-3-yl)-oxo-acetyl chloride and 2-(6-ethoxy-1-methyl-1H-indol-3-yl)-acetimidic acid isopropyl ester hydrochloride.

pp) 3-(4-Bromo-1-methyl-1H-indol-3-yl)-4-(6-ethoxy-1-methyl-1H-indol-3-yl)-pyrrole-2,5-dione; mp=>266° C. was prepared from (4-bromo-1-methyl-1H-indol-3-yl)-oxo-acetyl chloride and 2-(6-methoxy-1-methyl-1H-indol-3-yl)-acetimidic acid isopropyl ester hydrochloride.

qq) 3-(6-Ethoxy-1-methyl-1H-indol-3-yl)-4-(1-methyl-6-nitro-1H-indol-3-yl)-pyrrole-2,5-dione; mp=260° C. was prepared from (1-methyl-6-nitro-1H-indol-3-yl)-oxo-acetyl chloride and 2-(6-ethoxy-1-methyl-1H-indol-3-yl)-acetimidic acid isopropyl ester hydrochloride.

rr) 3-{6-[2-(2-Ethoxy-ethoxy)-ethoxy]-1-methyl-1H-indol-3-yl}-4-(1-methyl-6-nitro-1H-indol-3-yl)-pyrrole-2,5-dione; mp=124° C. was prepared from {6-[2-(2-ethoxy-ethoxy)-ethoxy]-1-methyl-1H-indol-3-yl}-oxo-acetyl chloride and 2-(1-methyl-6-nitro-1H-indol-3-yl)-acetimidic acid isopropyl ester hydrochloride.

ss) N-{1-Methyl-3-[4-(1-methyl-6-nitro-1H-indol-3-yl)-2,5-dioxo-2,5-dihydro-1H-pyrrol-3-yl]-1H-indol-3-yl}-acetamide was prepared from (6-acetylamino-1-methyl-1H-indol-3-yl)-oxo-acetyl chloride and 2-(1-methyl-6-nitro-1H-indol-3-yl)-acetimidic acid isopropyl ester hydrochloride.

EXAMPLE 3

3-(1-methyl-6-methylsulfanyl-1H-indol-3-yl)-4-(1-methyl-6-nitro-1H-indol-3-yl)-pyrrole-2,5-dione a) To a solution of sodium methoxide prepared from Na metal (8.65 g, 0.38 m) in methanol (200 mL) at 0–5° C., was added a solution of 4-(methylthio)benzaldehyde (12.6 ml, 94.7 mmol) and methyl azidoacetate (44 g, 0.382mol) in methanol (30 mL). After stirring at the same temperature for 3 hours, the suspension was diluted with $H_2O$ (300 mL). The solids were filtered, washed with water and dried under vacuum to provide 19.4 g (82.0%) of methyl-2-azido-3-(4-methylthio-phenyl)propenoate as a yellow solid.

A solution of methyl-2-azido-3-(4-methylthiophenyl)-propenoate (20.6 g, 83 mmol) in xylene (200 ml) was added dropwise to boiling xylene (250 ml) over a period of 2 hours. The reaction mixture was allowed to heat at reflux temperature for an additional 2 hours, then cooled slowly and placed in a freezer overnight. The solids were filtered, washed with a small amount of $CH_2Cl_2$/hexane (1:3) and dried to give 11.2 g (61.0%) of methyl-6-methylsulfanyl-1H-indole-2-carboxylate.

A mixture of methyl-6-methylsulfanyl-1H-indole-2-carboxylate (11.2 g, 51 mmol) and 2N NaOH (125 ml) was heated to reflux temperature for 30 minutes. The clear solution was cooled, and extracted with EtOAc. The aqueous fraction was acidified with concentrated HCl to pH=1, and the precipitate which formed, was filtered and dried to give 6-Methylsulfanyl-1H-indole-2-carboxylic acid (9.6 g, 91.0%).

A mixture of 6-methylsulfanyl-1H-indole-2-carboxylic acid (9.6 g, 46 mmol), Cu powder (2.1 g, 33 mmol) and quinoline (100 ml) was heated at 215° C. for 3 hours. The mixture was cooled to room temperature, filtered through celite, and filtrate diluted with H$_2$O (500 mL). The cooled mixture was acidified with concentrated HCl (pH=1), and extracted with EtOAc. The organic fraction was washed with saturated NaCl solution, dried over MgSO$_4$, filtered and evaporated to give 6-Methyl-sulfanyl-1H-indole (6.8 g, 90%) after purification by flash column chromatography.

b) In a manner similar to that of Example 1(f), 2-(1-methyl-6-nitro-1H-indol-3-yl)-acetimidic acid isopropyl ester hydrochloride was prepared from (1-methyl-6-nitro-1H-indol-3-yl)-acetonitrile.

c) In a manner similar to that of Example 1(g), 3-(1-methyl-6-methylsulfanyl-1H-indol-3-yl)-4-(1-methyl-6-nitro-1H-indol-3-yl)-pyrrole-2,5-dione; mp=273–275° C. was prepared from (1-methyl-6-methylsulfanyl-1H-indol-3-yl)-oxo-acetyl chloride and 2-(1-methyl-6-nitro-1H-indol-3-yl)-acetimidic acid isopropyl ester hydrochloride.

EXAMPLE 4

3,4-Bis-(6-Methoxy-1-Methyl-Indol-3yl)-Pyrrole-2,5-Dione a) A solution of CH$_3$MgI (15 mmol, in Et$_2$O) was treated with a solution of 6-methoxy-1H-indole (2.21 g, 15 mmol) in toluene (20 mL). After stirring at room temperature for 3.5 hours, a solution of 3,4-dichloro-1-methylmaleimide (1.2 g, 6.5 mmol) in toluene (20 mL) was added dropwise to the suspension. After heating at reflux temperature for 2 hours, the mixture was cooled to room temperature, and treated with NaH (26 mmol). After heating the mixture at reflux temperature for 15 hours, the mixture was poured into 20% aqueous citric acid solution and extracted with EtOAc (100 ml×3). The combined organic fractions were washed with H$_2$O, saturated NaCl solution, and dried over MgSO$_4$. After filtration, and evaporation of the solvent, the residue was purified by flash column chromatography to afford 3,4-Bis-(6-Methoxy-1H-indol-3-yl)-1-methyl maleimide (3.65 g, 70%).

b) A solution of 3,4-Bis-(6-methoxy-1H-indol-3-yl)-1-methylmaleimide (0.97 g, 24 mmol) and N-methyl pyrrolidinone (25 mL) was treated with K$_2$CO$_3$(5.8 g, 42 mmol), and CH$_3$I (2.13 g, 15 mmol). After stirring for 15 hours, volatile liquids were removed, and the product precipitated by addition of H$_2$O (50 mL), collected and washed with H$_2$O (20 mL) and hexane (lOmL) to afford 3,4-Bis-(6-methoxy-1-methyl-indol-3-yl)-1-methylmaleimide (1 g, 96%).

c) A suspension of 3,4-Bis-(6-methoxy-1-methyl-indol-3-yl)-1-methylmaleimide (0.96 g, 2.23 mmol) in ethanol (30 mL) was treated with 5N KOH (30 mL) and heated to reflux temperature until tlc indicated the disappearance of starting material (approximately 22 hours). After removal of most of the ethanol, the pH of the solution was adjusted to 2 by addition of 2N HCl. Solids were collected by filtrations and washed with H$_2$O. This material (0.92 g) in DMF (16 mL) was treated with pre-mixed solution of 1,1,1,3,3,3-hexamethyldisilazane (4 g, 25 mmol) and CH$_3$OH (4 g, 12.5 mmol). After stirring the solution for 15 hours at room temperature, H$_2$O (20 mL) was added and the solids which precipitated were collected by filtration and further washed with H$_2$O to afford 3,4-Bis-(6-methoxy-1-methyl-indol-3-yl)-pyrrole-2,5-dione; mp 257–258° C.

EXAMPLE 5

The following three procedures exemplify methodology to reduce nitro bis-indolymaleimides to amino bis-indolylmaleimides.

a) 3-[4-(6-Amino-1-methyl-1H-indol-3-yl)-2,5-dioxo-2,5-dihydro-1H-pyrrol-3-yl]-1-methyl-1H-indole-6-carbonitrile 3-(6-cyano-1-methyl-1H-indol-3-yl)-4-(1-methyl-6-nitro-1H-indol-3-yl)-pyrrole-2,5-dione (9.0 g, 21 mmole) was suspended in ethanol (1.8 L) and treated with tin (II) chloride dihydrate (35 g, 156 mmole). This was mechanically stirred for 16 h at reflux. The reaction was cooled and reduced in volume to 1L. This was poured into a mixture of ethyl acetate (2 L) and saturated sodium bicarbonate solution (1 L) and well mixed. The organic layer was decanted and washed with saturated sodium bicarbonate solution, dried over magnesium sulfate, filtered, evaporated, and then purified by flash column chromatography (ethyl acetate). The product was further purified by crystalization from tetrahydrofuran/hexane to provide 6.5 g of 3-[4-(6-amino-1-methyl-1H-indol-3-yl)-2,5-dioxo-2,5-dihydro-1H-pyrrol-3-yl]-1-methyl-1H-indole-6-carbonitrile; mp 255–260° C.

b) 3,4-Bis-(6-amino-1H-indol-3-yl)-pyrrole-2,5-dione 3,4-Bis-(1-methyl-6-nitro-1H-indol-3-yl)-pyrrole-2,5-dione (50 mg, 0.11 mmole), as prepared in Example 2 g, was dissolved in N,N-dimethylformamide (10 mL), a catalytic amount of activated Raney Nickel was added and the reaction was shaken on a Parr Hydro-genator at 45 psi. for 20 hr. The reaction mixture was filtered through a bed of celite with ethyl acetate and concentrated. The product was purified by recrystallization from acetone and hexane to give 3,4-bis-(1-methyl-6-amino-1H-indol-3-yl)-pyrrole-2,5-dione (35 mg).

c) 3-(6-Amino-1-methyl-1H-indol-3-yl)-4-(6-fluoro-1-methyl-1H-indol-3-yl)-pyrrole-2,5-dione To a suspension of 1.0 g (2.39 mmole) of 3-(6-fluoro-1-methyl-1H-indol-3-yl)-4-(1-methyl-6-nitro-1H-indol-3-yl)-pyrrole-2,5-dione in 20 ml of ethanol and 10 mL of tetrahydrofuran was added 0.55 g of 10% Pd/C and 0.54 mL of 5% hydrochloric acid. The mixture was cooled in an ice bath, and 0.54 mL (14.34 mmole) of hydrazine hydrate (85%) was added dropwise over 5 min. The reaction mixture was allowed to warm to room temp as it was stirred for two hours. The catalyst was removed by filtration over Celite. The filtrate was evaporated and the residue was crystallized from ethyl acetate/tetrahydrofuran/hexane to give 708 mg (76%) of )3-(6-amino-1-methyl-1H-indol-3-yl)-4-(6-fluoro-1-methyl-1H-indol-3-yl)-pyrrole-2,5-dione.

EXAMPLE 6

Following the indicated general procedure outlined in Example 5, the following compounds were prepared:

a) 3-(6-Amino-1-methyl-1H-indol-3-yl)-4-(6-chloro-1-methyl-1H-indol-3-yl)-pyrrole-2,5-dione was prepared from 3-(6-chloro-1-methyl-1H-indol-3-yl)-4-(1-methyl-6-nitro-1H-indol-3-yl)-pyrrole-2,5-dione utilizing procedure c) in Example 5.

b) 3-(6-Amino-1-methyl-1H-indol-3-yl)-4-(6-bromo-1-methyl-1H-indol-3-yl)-pyrrole-2,5-dione was prepared from 3-(6-bromo-1-methyl-1H-indol-3-yl)-4-(1-methyl-6-nitro-1H-indol-3-yl)-pyrrole-2,5-dione utilizing procedure a) in Example 5.

c) 3-[4-(6-Amino-1-methyl-1H-indol-3-yl)-2,5-dioxo-2,5-dihydro-1H-pyrrol-3-yl] -1-methyl-1H-indole-6-carboxylic acid methyl ester was prepared from 3-[4-(1-methyl-6-nitro-1H-indol-3-yl)-2,5-dioxo-2,5-dihydro-1H-pyrrol-3-yl]-1-methyl-1H-indole-6-carboxylic acid methyl ester utilizing procedure a) in Example 5.

d) 3-(6-Amino-1-methyl-1H-indol-3-yl)-4-(1-methyl-6-methylsulfanyl-1H-indol-3-yl)-pyrrole-2,5-dione was prepared from 3-(1-Methyl-6-methylsulfanyl-1H-indol-3- yl)- 4-(1-methyl-6-nitro-1H-indol-3-yl)-pyrrole-2,5-dione utilizing procedure a) in Example 5.

e) 3-(6-Amino-1-methyl-1H-indol-3-yl)-4-(1,6-dimethyl-1H-indol-3-yl)-pyrrole-2,5-dione was prepared from 3-(1,6-dimethyl-1H-indol-3-yl)-4-(1-methyl-6-nitro-1H-indol-3-yl)-pyrrole-2,5-dione utilizing procedure c) in Example 5.

f) 3-(6-Amino-1-methyl-1H-indol-3-yl)-4-(6-methoxy-1-methyl-1H-indol-3-yl)-pyrrole-2,5-dione was prepared from 3-(6-methoxy-1-methyl-1H-indol-3-yl)-4-(1-methyl-6-nitro-1H-indol-3-yl)-pyrrole-2,5-dione utilizing procedure b) in Example 5.

EXAMPLE 7

General procedure for preparing hydrochloride salts of amino bis indolymaleimides:

3-(6-Amino-1-methyl-1H-indol-3-yl)-4-(6-fluoro-1-methyl-1H-indol-3-yl)-pyrrole-2,5-dione hydrochloride salt To a mixture of 75 mg (0.193 mmole) of 3-(6-amino-1-methyl-1H-indol-3-yl)-4-(6-fluoro-1-methyl-1H-indol-3-yl)-pyrrole-2,5-dione in 2 mL of acetonitrile was added 10 mL of water, precipitating solids. To this mixture was added 0.64 mL (0.772 mmole) of 1.2M hydrochloric acid, forming a clear solution. After 10 min. the mixture was concentrated to dryness. It was redissolved in acetonitrile and concentrated to dryness. The residue was dissolved in 4 mL of water and lyophilized overnight to give 80 mg (97%) of 3-(6-amino-1-methyl-1H-indol-3-yl)-4-(6-fluoro-1-methyl-1H-indol-3-yl)-pyrrole-2,5-dione hydrochloride salt.

In a similar manner, the hydrochloride salts of other amines were prepared.

EXAMPLE 8

3-(6-Amino-1-methyl-1H-indol-3-yl)-4-(1-methyl-6-nitro-1H-indol-3-yi)-pyrrole-2,5-dione a) 5.29 gms of 1-methyl-6-nitroindole and 7.5 gms 10% Pd/C in 400 mL ethanol was treated with 30 mL 2N hydrochloric acid and 2.04 mL 85% hydrazine hydrate at 0° C. It was stirred at room temperature and treated portionwise with 1 mL hydrazine hydrate. The mixture was filtered over a bed of celite and washed with ethanol. The filtrate was concentrated to 50 mL and cooled to 0° C. for 1 h. Fine needle crystals were filtered off as hydrazine hydro-chloride. The filtrate was concentrated to 25 mL and refrigerated. Filtered to remove more by-product. The filtrate was treated portionwise with cold 6N hydrochloric acid and concentrated to about 25 mL, refrigerated and tan crystals of product collected. The filtrate was again concentrated to about 10 mL ethanol and again treated with cold 6N hydrochloric acid, concentrated and redissolved in 5 mL ethanol and hexanes to further crystallize product. The tan crystals are collected and the combined yield was 2.80 gms of 6-amino-1-methylindole hydrochloride.

b) 2.5 gms of 6-amino-1-methylindole hydrochloride was taken into 30 mL dry pyridine and treated with 1.93 mL of trifluoroacetic anhydride at 0° C. It was stored in the refrigerator overnight. It was taken into cold water and extracted with ethyl acetate and washed with cold 5% phosphoric acid and 5% brine. The organics were dried over magnesium sulfate and the concentrated crude product was further purified by flash silica chromatography. Product was crystallyzed from methylene cholride/hexanes to give 1.1 gms of 1-methyl-6-trifluoroacetylaminoindole.

c) 200 mg of 1-methyl-6-trifluoroacetylaminoindole was taken into 5 mL ether and cooled to 0° C. It was treated with 0.485 mL 2.0 M oxalyl chloride/methylene dichloride and stirred at 0° C. for 2 h. The yellow crystals were collected and washed with ether and dried in vacuo to yield 240 mg of (6-trifluoroacetylamino-1-methyl-1H-indol-3-yl)-oxo-acetyl chloride.

d) 240 mg of (6-trifluoroacetylamino-1-methyl-1H-indol-3-yl)-oxo-acetyl chloride and 181 mg of 2-(1-methyl-6-nitro-1H-indol-3-yl)-acetimidic acid isopropyl ester hydrochloride were stirred in methylene chloride with 494 mg triethylamine at 0° C. for 2 hrs, then at room temperature overnight. The reaction mix was diluted with methylene chloride and washed with cold 0.5N hydrochloric acid and 5% brine. It was back extracted with methylene chloride and the organic extracts were passed over a plug of magnesium sulfate and concentrated. The crude residue was taken into methylene chloride and treated with 244 mg of p-toluene sulfonic acid for 5 hrs at room temperature. It was diluted with methylene chloride and a few drops of methanol was added to solubilize. It was washed with 10% sodium bicarbonate and water and back extracted with methylene chloride. The organics were dried over magnesium sulfate and concentrated. The crude material was further purified by prep LC (20% ethyl acetate/methylene chloride) to yield 48 mg of N-{1-methyl-3-[4-(1-methyl-6-nitro-1H-indol-3-yl)-2,5-dioxo-2,5-dihydro-1H-pyrrol-3-yl]-1H-indol-3-yl}-trifluoroacetamide as a red-orange solid.

e) 120 mg of N-{1-methyl-3-[4-(1-methyl-6-nitro-1H-indol-3-yl)-2,5-dioxo-2,5-dihydro-1H-pyrrol-3-yl]-1H-indol-3-yl}-trifluoro-acetamide was taken into 8 mL water/methanol (1/1) and treated with 240 mg potassium carbonate and warmed to 45° C. for 5 hours. It was cooled to room temperature and taken into methylene chloride and washed with water and back extracted with methylene chloride. The organics were dried over magnesium sulfate and filtered and concentrated to near dryness. 25 niL acetonitrile was added and it was concentrated to 5 mL and diluted with 25 mL acetonitrile/water (1/1) and acidified with 0.25 mL 1.0 N hydro-chloric acid. It was concentrated to remove acetonitrile and lyophilized to yield 50 mg of 3-(6-Amino-1-methyl-1H-indol-3-yl)-4-(1-methyl-6-nitro-1H-indol-3-yl)-pyrrole-2,5-dioneas a red orange solid.

EXAMPLE 9

N-(1-methyl-3-[4-(1-methyl-6-nitro-1H-indol-3-yl)-2,5-dioxo-2,5-dihydro-1H-pyrrol-3-yl]-1H-indol-3-yl) acetamide (6-Acetylamino-1-methyl-1H-indol-3-yl)-oxo-acetyl chloride was prepared from 6-Amino-1-methyl-1H-indole utilizing procedures similar to those described in b) and c), Example 8. It was then converted to N-(1-methyl-3-[4-(1-methyl-6-nitro-1H-indol-3-yl)-2,5-dioxo-2,5-dihydro-1H-pyrrol-3-yl]-1H-indol-3-yl)acetamide utilizing a procedure similar to that described in Example 8d.

EXAMPLE 10

3-(6-Amino-1-methyl-1H-indol-3-yl)-4-(6-[4-azido-3-iodo-phenyl)-2-oxo-butyl]-1-methyl-1H-indol-3-yl)-pyrrole-2,5-dione 3,4-Bis-(1-methyl-6-amino-1H-indol-3-yl)-pyrrole-2,5-dione (40 mg, 0.1 mmole) was dissolved in tetrahydrofuran (3 mL) and cooled to 0° C. 3-(4-Azido-3-iodo-phenyl)-propionic acid (29.6 mg, 0.09 mmole) was added followed by N-hydroxybenztriazole (16 mg, 0.1 mmole) and diisopropylcarbodiimide (16 µl, 0.1 mmole). The reaction was stirred at 0° C. for 5 hr. The reaction was concentrated and purified by column chromatography in 3% methanol /methylene chloride to give 3-(6-amino-1-methyl-1H-indol-3-yl)-4-(6-[4-azido-3-iodo-phenyl]-2-oxo-butyl]-1-methyl-1H-indol-3-yl)-pyrrole-2,5-dione (18.7 mg, 29%).

EXAMPLE 11

In a manner similar to that described in Example 10, the following compounds were prepared:
a) 3-(6-Fluoro-1-methyl-1H-indol-3-yl)-4-(6-[4-azido-3-iodo-phenyl)-2-oxo-butyl]-1-methyl-1H-indol-3-yl)-pyrrole-2,5-dione was prepared from 3-(6-fluoro-1-methyl-1H-indol-3-yl)-4-(1 -methyl-6-amino-1H-indol-3-yl)-pyrrole-2,5-dione.
b) 3-(6-Methoxy-1-methyl-1H-indol-3yl)-4-(6-[4-azido-3-iodo-phenyl)-2-oxo-butyl]-1-methyl-1H-indol-3-yl)-pyrrole-2,5-dione was prepared from 3-(6-methoxy-1-methyl-1H-indol-3-yl)-4-(1-methyl-6-amino-1H-indol-3-yl)-pyrrole-2,5-dione.
c) N-{3-[4-(6-Formylamino-1-methyl-1H-indol-3-yl)-2,5-dioxo-2,5-dihydro-1H-pyrrol-3-yl]-1-methyl-1H-indol-6-yl}-formamide was prepared from 3,4-bis-(1-methyl-6-amino-1H-indol-3-yl)-pyrrole-2,5-dione and formic acid.
d) N-{3-[4-(6-Methoxy-1-methyl-1H-indol-3-yl)-2,5-dioxo-2,5-dihydro-1H-pyrrol-3-yl]-1-methyl-1H-indoe -6-yl a -foolamide was prepared from 3-(6-methoxy-5-methyl-1H-indol-3-yl)-4-(1-m ethyl-6-amino-1H-indol-3-yl)-pyrrole-2,5-dione and formic acid.

EXAMPLE 12

N-{3-[4-(6-Acetylamino-1-methyl-1H-indol-3-yl)-2,5-dioxo-2,5-dihydro-1H-pyrrol-3-yl]-1-methyl-1H-indol-6-yl}-acetamide 3,4-Bis-(1-methyl-6-amino-1H-indol-3-yl)-pyrrole-2,5-dione (50 mg, 0.13 mmole) was dissolved in tetrahydrofuran (2.5 mL) and cooled to 0° C. Triethylamine (38.5 µl, 0.27 mm) was added followed by acetyl chloride (19.4 pl, 0.27 mmole). The reaction was stirred for 30 min, then concentrated. The reaction mixture was dissolved in chloroform, washed with 0.1 N hydrochloric acid and the organic was dried over magnesiun sulfate, filtered and concentrated. The product was purified by column chromatography in 5% methanol/ethyl acetate to give N-{3-[4-(6-acetylamino-1-methyl-1H-indol-3-yl)-2,5-dioxo-2,5-dihydro-1H-pyrrol-3-yl]-1-methyl-1H-indol-6-yl}-acetamide (14 mg, 23%).

EXAMPLE 13

N-{3-[4-(6-Methoxy-1-methyl-1H-indol-3-yl)-2,5-dioxo-2,5-dihydro-1H-pyrrol-3-yl]-1-methyl-1H-indol-6-yl}-acetamide In a manner similar to that described in Example 12, N-{3-[4-(6-Methoxy-1-methyl-1H-indol-3-yl)-2,5-dioxo-2, 5-dihydro-1H-pyrrol-3-yl]-1-methyl-1H-indol-6-yl}-acetamide from 3-(6-methoxy-1-methyl-1H-indol-3-yl)-4-(1-methyl-6-amino-1H-indol-3-yl)-pyrrole-2,5-dione.

EXAMPLE 14

3-(6-Methoxy-1-methyl-1H-indol-3-yl)-4-(1-methyl-6-methyl-amino-1H-indol-3-yl)-pyrrole-2,5-dione a) 6-Aminoindole was prepared from 6-nitroindole in a manner similar to that described in Example 5b.
b) N-Methyl-(1-methyl-1H-indol-6-yl)-amine was prepared from 6-amino indole in a manner similar to that described in Example 1 a. c) Methyl-(1-methyl-1H-indol-6-yl)-amine (50 mg, 0.33 mmole) was dissolved in methylene chloride (2 mL) and cooled to 0° C. Triethylamine (55 µl, 0.39 mmole) was added followed by benzylchloroformate (52 µL, 0.39 mmnole). The reaction was stirred at room temperature for 1 hr. The reaction mixture was washed with 0.1 N hydrochloric acid and the organic was dried over magnesium sulfate, filtered and concentrated. The product was purified by column chromatography in 25% ethyl acetate/hexane to give methyl-(1-methyl-1H-indol-6-yl)-carbamic acid benzyl ester (67 mg, 73%).
d) (3-Chlorocarbonecarbonyl-1-methyl-1H-indol-6-yl)-methyl-carbamic acid benzyl ester was prepared from methyl-(1-methyl-1H-indol-6-yl)-carbamic acid benzyl ester in a procedure similar to that described in Example 1b.
e) 2-(6-Methoxy-1-methyl-1H-indol-3-yl)-acetimidic acid isopropyl ester hydrochloride, prepared as in Example 1 f, and (3-chlorocarbonecarbonyl-1-methyl-1H-indol-6-yl)-methyl-carbamic acid benzyl ester were coupled in a manner similar to that described in Example 1 g to give {3-[4-(6-methoxy-1-methyl-1H-indol-3-yl)-2,5-dioxo-2, 5-dihydro-1H-pyrrol-3-yl]-1-methyl-1H-indol-6yl }-methyl-carbamic acid benzyl ester.
f) (3-[4-(6-Methoxy-1-methyl-1H-indol-3-yl)-2,5-dioxo-2, 5-dihydro-1H-pyrrol-3-yl]-1-methyl-1H-indol-3-yl}-methyl-carbamic acid benzyl ester (26mg, 0.048 mmole), was dissolved in toluene (4 mL). Pd/C (10 mg×10%, 0.009 mmole) was added and reaction was shaken on a Parr Hydrogenator at 50 psi. for 13 h. The crude reaction mixture was filtered through a bed of Celite and concentrated to give 3-(6-methoxy-1-methyl-1H-indol-3-yl)-4-(1-methyl-6-methylamino-1H-indol-3-yl)-pyrrole-2,5-dione (16 mg, 81%).

TABLET FORMULATION

| Item | Ingredients | mg/Tablet | | | | | |
|------|-------------|-----------|---|---|---|---|---|
|      |             | 5 mg | 25 mg | 100 mg | 250 mg | 500 mg | 750 mg |
| 1 | Compound A | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
|   | Total Weight | 120 | 120 | 150 | 300 | 600 | 900 |

Compound A represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.

4. Pass the granulation from Step 3 through a suitable milling equipment.
5. Add the Item 5 to the milled granulation Step 4 and mix for 3 minutes.
6. Compress the granulation from Step 5 on a suitable press.

EXAMPLE 16

| | CAPSULE FORMULATION | | | | | |
|---|---|---|---|---|---|---|
| | | mg/Tablet | | | | |
| Item | Ingredients | 5 mg | 25 mg | 100 mg | 250 mg | 500 mg |
| 1 | Compound A | 5 | 25 | 100 | 250 | 500 |
| 2 | Hydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Manufacturing Procedure:
1. Mix Items 1, 2 and 3 in a suitable mixer for 15 minutes.
2. Add Items 4 & 5 and mix for 3 minutes.
3. Fill into a suitable capsule.

EXAMPLE 17

| | INJECTION SOLUTION/EMULSION PREPARATION | |
|---|---|---|
| Item | Ingredient | mg/mL |
| 1 | Compound A | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Manufacturing Procedure:
1. Dissolve item 1 in item 2
2. Add items 3, 4 and 5 to item 6 and mix until until dispersed, then homogenize.
3. Add the solution from step 1 to the mixture from step 2 and homogenize until the dispersion is translucent.
4. Sterile filter through a 0.2 um filter and fill into vials.

EXAMPLE 18

| | INJECTION SOLUTION/EMULSION PREPARATION | |
|---|---|---|
| Item | Ingredient | mg/mL |
| 1 | Compound A | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Manufacturing Procedure:
1. Dissolve item 1 in item 2
2. Add items 3, 4 and 5 to item 6 and mix until until dispersed, then homogenize.
3. Add the solution from step 1 to the mixture from step 2 and homogenize until the dispersion is translucent.
4. Sterile filter through a 0.2 um filter and fill into vials.

What is claimed is:

1. A compound of the formula

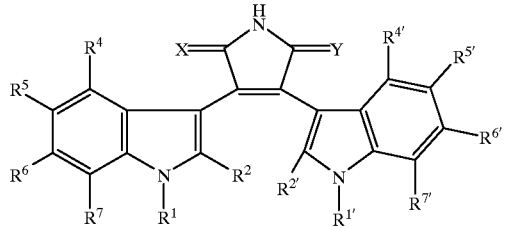

wherein $R^1$ and $R^{1'}$ are independently alkyl, aryl, alkenyl or alkynyl;

$R^2$ and $R^{2'}$ are independently hydrogen or alkyl;

$R^4$, $R^5$, $R^7$, $R^{4'}$, $R^{5'}$, and $R^{7'}$ each are hydrogen, $R^6$ and $R^{6'}$ are independently nitro, alkoxy, alkyl, halogen, cyano,

$CO_2R^9$, $CH_2OR^{10}$, CHO, $CH_2NR^{11}R^{12}$, $CON(R^{13})_2$, alkylthio or aralkyloxy;

$R^8$ is alkyl or aryl;

$R^9$ is alkyl or aryl;

$R^{10}$ is hydrogen, alkyl or aryl;

$R^{11}$ and $R^{12}$ are independently hydrogen, alkyl, aryl, aralkyl or acyl;

$R^{13}$ is hydrogen, alkyl, aryl or aralkyl; and one of X and Y signifies O and the other signifies O, S, (H,OH) or (H,H); or a pharmaceutically acceptable salt of an acidic compound of formula I or a pharmaceutically acceptable salt of a basic compound of formula I wherein alkyl contains a maximum of 10 carbon atoms;

alkenyl contains 2 to 5 carbons;

acyl contains a maximum of 10 carbon atoms, and aryl is an unsubstituted phenyl group or a phenyl group substituted by one, two or three substituents which substituents are independently halogen, alkyl, hydroxy, benzyloxy, alkoxy, haloalkyl, nitro, amino or cyano.

2. A compound of claim 1, wherein $R^8$ and $R^9$ are independently alkyl, $R^{10}$ is hydrogen or alkyl, $R^{11}$ and $R^{12}$ are hydrogen or alkyl and $R^{13}$ is hydrogen or alkyl.

3. A compound of claim 2, wherein $R^8$ and $R^9$ are methyl.

4. A compound of claim 2, wherein $R^{10}$ is methyl.

5. A compound of claim 2, wherein $R^{11}$, $R^{12}$ and $R^{13}$ are alkyl.

6. A compound of claim 1, wherein $R^1$ and $R^{1'}$ are alkyl, and $R^2$ and $R^{2'}$ are hydrogen.

7. A compound of the formula

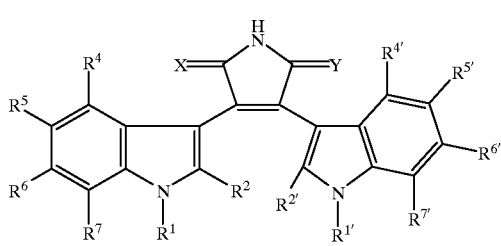

wherein $R^1$ and $R^{1'}$ are independently alkyl;

$R^2$ and $R^{2'}$ are each hydrogen;

$R^6$ is amino, acylamino, monoalkyl amino or dialkylamino, $R^4$, $R^5$, $R^7$, $R^{4'}$, $R^{5'}$, $R^{6'}$, and $R^{7'}$ each independently are hydrogen,

$CO_2R^9$, $CH_2OR^{10}$, CHO, $CH_2NR^{11}R^{12}$, $CON(R^{13})_2$, halogen, cyano, aryl, alkyl, hydroxy, alkoxy, aryloxy, haloalkyl, nitro, amino, aralkyloxy, acylamino, monoalkylamino, dialkylamino, thio, alkylthio, alkylsulphinyl, alkylsulphonyl, arylsulphinyl, azide, phosphate or phosphonate provided that at least one of $R^{4'}$, $R^{5'}$, and $R^{6'}$ are other than hydrogen;

$R^8$ is alkyl or aryl;

$R^9$ is alkyl or aryl;

$R^{10}$ is hydrogen, alkyl or aryl;

$R^{11}$ and $R^{12}$ are independently hydrogen, alkyl, aryl, aralkyl or acyl;

$R^{13}$ is hydrogen, alkyl, aryl or aralkyl; and one of X and Y signifies O and the other signifies O, S, (H,OH) or (H,H); or a pharmaceutically acceptable salt of an acidic compound of formula I or a pharmaceutically acceptable salt of a basic compound of formula I wherein alkyl contains a maximum of 10 carbon atoms;

alkenyl contains 2 to 5 carbons;

acyl contains a maximum of 10 carbon atoms, and aryl is an unsubstituted phenyl group or a phenyl group substituted by one two or three substituents which substituents are independently halogen, alkyl, hydroxy, benzyloxy, alkoxy, haloalkyl, nitro, amino or cyano.

8. A compound of claim 7, wherein $R^{6'}$ is

$CO_2R^9$, $CH_2OR^{10}$, CHO, $CH_2NR^{11}R^{12}$, $CON(R^{13})_2$, halogen, cyano, aryl, alkyl, hydroxy, alkoxy, aryloxy, haloalkyl, nitro, amino, aralkyloxy, acylamino, monoalkylamino, dialkylamino, thio, alkylthio, alkylsulphinyl, alkylsulphonyl, arylsulphinyl, azide, phosphate or phosphonate.

9. The compound 3-(6-amino-1-methyl-1H-indol-3-yl)-4-(6-fluoro-1-methyl-1H-indol-3-yl)-pyrrole-2,5-dione.

10. The compound 3-(6-amino-1-methyl-1H-indol-3-yl)-4-(6-bromo-1-methyl-1H-indol-3-yl)-pyrrole-2,5-dione.

11. The compound 3-(6-amino-1-methyl-1H-indol-3-yl)-4-(6-methoxy-1-methyl-1H-indol-3-yl)-pyrrole-2,5-dione.

12. The compound 3-(6-amino-1-methyl-1H-indol-3-yl)-4-(1-methyl-6-nitro-1H-indol-3-yl)-pyrrole-2,5-dione.

13. The compound 3-[4-(6-aniino-1-methyl-1H-indol-3-yl)-2,5-dioxo-2,5-dihydro-1H-pyrrol-3-yl]-1-methyl-1H-indole-6-carbonitrile.

14. The compound 3-(6-methoxy-1-methyl-1H-indol-3-yl)-4-(1-methyl-6-nitro-1H-indol-3-yl)-pyrrole-2,5-dione.

15. The compound 3-(6-benzyloxy-1-methyl-1H-indol-3-yl)-4-(1-methyl-6-nitro-1H-indol-3-yl)-pyrrole-2,5-dione.

16. The compound 3-(6-chloro-1-methyl-1H-indol-3-yl)-4-(1-methyl-6-nitro-1H-indol-3-yl)-pyriole-2,5-dione.

17. The compound 3-(1,6-dimethyl-1H-indol-3-yl)-4-(6-methoxy-1-methyl-1H-indol-3-yl)-pyrrole-2,5-dione.

18. The compound 3-(1,6-dimethyl-1H-indol-3-yl)-4-(1-methyl-6-nitro-1H-indol-3-yl)-pyrrole-2,5-dione.

19. The compound 3,4-bis-(6-methoxy-1-methyl-1H-indol-3-yl)-pyrrole-2,5-dione.

20. The compound 3-(6-fluoro-1-methyl-1H-indol-3-yl)-4-(1-methyl-6-nitro-1H-indol-3-yl)-pyrrole-2,5-dione.

21. The compound 3,4-bis-(1-methyl-6-nitro-1H-indol-3-yl)-pyrrole-2,5-dione.

22. The compound 3-(6-amino-1-methyl-1H-indol-3-yl)-4-(1-methyl-6-methylsulfanyl-1H-indol-3-yl)-pyrrole-2,5-dione.

23. The compound 3-(6-amino-1-methyl-1H-indol-3-yl)-4-(1,6-dimethyl-1H-indol-3-yl)-pyrrole-2,5-dione.

24. The compound N-{3-[4-(6-methoxy-1-methyl-1H-indol-3-yl)-2,5-dioxo-2,5-dihydro-1H-pyrrol-3-yl]-1-methyl-1H-indol-6-yl]}-acetamide.

25. The compound 3-(6-methoxy-1-methyl-1H-indol-3-yl)-4-(1-methyl-6-methyl-amino-1H-indol-3-yl)-pyrrole-2,5-dione.

26. The compound 3-[4-(1,6-dimethyl-1H-indol-3-yl)-2,5-dioxo-dihydro-1H-pyrrole-3-yl]-1-methyl-1H-indole-6-carbonitrile.

27. The compound 3-(1-methyl-6-methylfulfanyl-1H-indol-3-yl)-4-(1-methyl-6-nitro-1H-indol-3-yl)-pyrrole-2,5-dione.

28. The compound 3-{6-[2-(2-ethoxy-ethoxy)-ethoxy]-1-methyl-1H-indol-3-yl}-4-(1-methyl-6-nitro-1H-indol-3-yl)-pyrrole-2,5-dione.

* * * * *